(12) United States Patent
Park

(10) Patent No.: US 11,726,012 B2
(45) Date of Patent: Aug. 15, 2023

(54) COMPOSITION FOR BIOTISSUE CLEARING AND BIOTISSUE CLEARING METHOD USING SAME

(71) Applicant: BINAREE, INC., Daegu (KR)

(72) Inventor: Sun Hyun Park, Daejeon (KR)

(73) Assignee: Binaree, INC., Daegu (KR)

( * ) Notice: Subject to any disclaimer, the term of this patent is extended or adjusted under 35 U.S.C. 154(b) by 1048 days.

(21) Appl. No.: 16/462,973

(22) PCT Filed: Nov. 20, 2017

(86) PCT No.: PCT/KR2017/013168
§ 371 (c)(1),
(2) Date: Apr. 3, 2020

(87) PCT Pub. No.: WO2018/101663
PCT Pub. Date: Jun. 7, 2018

(65) Prior Publication Data
US 2020/0271553 A1 Aug. 27, 2020

(30) Foreign Application Priority Data
Nov. 29, 2016 (KR) .................. 10-2016-0160031

(51) Int. Cl.
*G01N 1/30* (2006.01)
*C07C 235/12* (2006.01)
*C07F 1/04* (2006.01)
*G01N 33/483* (2006.01)

(52) U.S. Cl.
CPC ............ *G01N 1/30* (2013.01); *C07C 235/12* (2013.01); *C07F 1/04* (2013.01); *G01N 33/4833* (2013.01); *G01N 2001/305* (2013.01)

(58) Field of Classification Search
None
See application file for complete search history.

(56) References Cited

U.S. PATENT DOCUMENTS

| 6,780,979 | B1 | 8/2004 | Deslys |
| 7,097,997 | B1 | 8/2006 | Deslys et al. |
| 10,571,371 | B2 * | 2/2020 | Marini ............... G01N 1/30 |
| 2015/0285718 | A1 | 10/2015 | Hatta et al. |

FOREIGN PATENT DOCUMENTS

| EP | 2199774 A1 | 6/2010 |
| EP | 2865685 A1 | 4/2015 |
| JP | 2003-066035 A | 3/2003 |
| JP | 2007097508 A | 4/2007 |
| JP | 2015049101 A | 3/2015 |
| KR | 10-1563826 B1 | 10/2015 |
| WO | 2014-025392 A1 | 2/2014 |
| WO | 2014-115206 A1 | 7/2014 |
| WO | 2015041755 A1 | 3/2015 |
| WO | 2016-023009 A1 | 2/2016 |

OTHER PUBLICATIONS

Rahman, Suhaila, et al. "Sarkosyl is a good regeneration reagent for studies on vacuolar-type ATPase subunit interactions in Biacore experiments." Analytical biochemistry 418.2 (2011): 301-303 (Year: 2011).*
Tainaka, Kazuki, et al. "Chemical principles in tissue clearing and staining protocols for whole-body cell profiling." Annu Rev Cell Dev Biol 32.1 (2016): 713-741. (Year: 2016).*
Iwanaga, Toshihiko, Takuya Kuchiiwa, and Masayuki Saito. "Histochemical demonstration of monocarboxylate transporters in mouse brown adipose tissue." Biomedical research 30.4 (2009): 217-225. (Year: 2009).*
Sacks, Harold, and Michael E. Symonds. "Anatomical locations of human brown adipose tissue: functional relevance and implications in obesity and type 2 diabetes." Diabetes 62.6 (2013): 1783-1790. (Year: 2013).*
Chung K et al., "Structural and molecular interrogation of intact biological systems", Nature, 2013, vol. 497(7449), pp. 332-337.
Raju Tomer et al., "Advanced Clarity for rapid and high-resolution imaging of intact tissues", Nat. Protoc., 2014, vol. 9, No. 7, pp. 1682-1697.
Lee, E. et al., "ACT-PRESTO: Rapid and consistent tissue clearing and labeling method for 3-dimensional (3D) imaging", Scientific Reports, 2016, vol. 6, Article No. 18631, pp. 1-13.
Ertürk A et al., "Three-dimensional imaging of solvent-cleared organs using 3DISCO", Nature Protocols, 2012, vol. 7, No. 11, pp. 1983-1995.
Douglas S. Richardson et al., "Clarifying Tissue Clearing", Cell., 2015, vol. 162(2), pp. 246-257.
Zhu, D. et al., 'Recent progress in tissue optial clearing', Laser & Photonics Reviews, 2013, vol. 7(5), pp. 732-757.
Baud, C., et al., "Purification of a functional mature region from a SecA-dependent preprotein", Protein Expression and Purification, 2005, 40(2): 336-339.
Setter, P.W., et al., "Tektin interactions and a model for molecular functions", Experimental Cell Research, 2006, 312(15): 2880-2896.
Labome, "Detergents: Triton X-100, Tween-20, and More", Mater Methods, 2013, 3: 163.

* cited by examiner

*Primary Examiner* — Robert J Yamasaki
(74) *Attorney, Agent, or Firm* — Riverside Law LLP

(57) ABSTRACT

The present invention relates to a composition for clearing a biotissue and a method for clearing a biotissue using thereof.

5 Claims, 21 Drawing Sheets

COMPOSITION FOR BIOTISSUE CLEARING AND BIOTISSUE CLEARING METHOD USING SAME

CROSS-REFERENCE TO RELATED APPLICATIONS

This application is the U.S. national phase application filed under 35 U.S.C. § 371 claiming benefit to International Patent Application No. PCT/KR2017/013168, filed on Nov. 20, 2017, which is entitled to priority under to Korean Patent Application No. 10-2016-0160031, filed Nov. 29, 2016, the disclosure of which is incorporated herein by reference in its entirety.

TECHNICAL FIELD

The present invention relates to a composition for clearing a biotissue and a method for clearing a biotissue using thereof.

BACKGROUND ART

Medical diagnostic technology using x-rays has been developed as a technology capable of three-dimensional observation and elaborate diagnosis by a three-dimensional reconstitution technology after two-dimensional scanning such as CT or MRI. Another technology for realizing a three dimensional image using ultrasound and the like instead of a light source has also been actively used for diagnosis. However, most technologies developed so far have a millimeter level macro-resolution, the three-dimensional measurement technologies at micro-level that can realize the analysis at cellular level have been relatively less developed, so that most cell level methods currently use the conventional two dimensional technologies. That is, the microstructure is analyzed by using a technology in which a biotissue such as a biopsy tissue or an autopsy tissue is fixed in a fixative solution, and embedded in paraffin or polymer, the sample is sliced into sections with a thickness of several micrometers or nanometers so as to let light or electronic waves pass through, and then transmission images are obtained by using an optical or electron microscope.

To obtain a three dimensional image using the micro-imaging technology, a confocal microscope needs to be used, and in this case, thickness information of tens of micrometers may be generally obtained. Roughly, the thickness is limited by the depth to which a light source may penetrate. However, since most of the significant structures in living tissues have a size of several hundreds of micrometers or more, only a part of the information may be obtained using the method as described above. Therefore, in order to obtain a thicker tissue image, there is a need for a series of processes in which sections having a thickness of tens of micrometers are prepared, followed by imaging of each by using a microscope, and then, the image is reconstructed. In particular, when a whole neuron of brain tissue is imaged, one neuron may stretch its axon up to a few meters, so that a series of processes in which the tissue has to be cut and attached again proceed, during which the problems that may occur are exponentially increased.

With the tissue clearing technology, the internal structure and protein distribution in the tissue may be confirmed without tissue damage, so that a technology of clearing tissues by various methods has been recently developed because the tissue clearing technology enables observation of the deeper inside of the tissue structure by overcoming the observation limit of the existing technology and access to the integral structure and molecular information from various systems.

As for the tissue clearing technology in the related art, the antigen conservation in the tissue treated by Spatleholz, BABB, Scale S, and iDISCO methods as a tissue clearing process using an organic solvent and an active clarity technology (ACT) method as a polymer injection method has been reported. Except for the ACT, all other methods have a problem in that fluorescence and antigen conservation are reduced. The ACT has an antigen conservation of 90% or more, and shows much higher conservation than other methods additionally requiring a hydrogel polymer binding to a fixed protein, such as the CLARITY. However, since a strong tissue fixation process causes the loss of antigenicity, a problem such as a decrease in available antibodies needs to be considered, so that there is a need for improvement of various technologies.

Further, the 'CLARITY'-based technology as a tissue clearing method recently developed uses a method of selectively eliminating only lipids after constructing a kind of net supporter in a tissue to hold materials important for diagnosis such as DNA or proteins by adding a hydrogel to the tissue (see Non-Patent Document 1, Chung K, et al. (2013) Nature 497(7449): 332-337).

However, according to the above method, the hydrogel supporter infiltrates into a tissue, and when the concentration of hydrogel is increased, the tissue becomes harder because the degree of binding to a protein is increased and a more compact net structure is produced. In contrast, once the tissue gets harder, it is difficult for the lipid to escape by using a surfactant, indicating that the time taken to clear the tissue is prolonged. In addition, the above method has a problem in that air and dark particles are deposited on the tissue surface, or tissues are discolored yellow.

Furthermore, the above method requires a lot of additional equipment and the process is very complicated. For example, in order to clear only the brain, it costs at least 30,000,000 Korean Won. Besides, since the method can clear only one brain at a time, the method is not economical and can be time-consuming. The bigger problem is that it is difficult for a stain using antibodies to pass through a polyacrylamide net structure.

Therefore, to obtain the protein distribution information in tissue, the physical diffusion ability of an antibody needs to be increased, in consideration of the conservation degree of antigenicity and the permeability of the antibody in tissues after tissue clearing, but when the tissues are hard and have many connective tissues, the diffusion rate of the antibody is decreased remarkably, so that a new technique to overcome the problems is required.

As described above, in research in the related art, the process thereof is not only complicated but also costly and time-consuming for clearing tissues. Therefore, there is a need for a technology capable of clearing not only the brain, but also various tissues by simplifying the process, reducing the costs, and optimizing antibody staining.

Thus, while conducting studies on a technology for clearing a biotissue, the present inventors have found that a composition for clearing a biotissue and a method for clearing a biotissue using the same according to the present invention do not need expensive electrophoresis equipment and expensive solutions, and not only can be applied to various biotissues such as the brain, liver, lungs, kidneys, intestines, heart, muscle, and blood vessels, without damaging any of the biotissues, but also can improve the clarity of the biotissue without bubble formation, discoloration, and dark sediment, and enable antibody staining in the cleared tissues, so that the composition and the method can be usefully used to elucidate the causes of various diseases by the structural images of the biotissue and to establish a treatment method for a disease, thereby completing the present invention.

DISCLOSURE

Technical Problem

An object of the present invention is to provide a composition for clearing a biotissue.
Another object of the present invention is to provide a method for clearing a biotissue.

Technical Solution

To achieve the above objects, the present invention provides a composition for clearing a biotissue, comprising an amino acid represented by the following Formula 1, or a salt thereof.

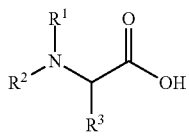

[Formula 1]

(in Formula 1,
$R^1$ is hydrogen or a $C_1$-$C_2$ alkyl,
$R^2$ is hydrogen or a straight-chained or branched $C_8$-$C_{20}$ alkylcarbonyl or $C_8$-$C_{20}$ alkenylcarbonyl, and
$R^3$ represents hydrogen or a side chain of an essential amino acid).

Further, the present invention provides a method for clearing a biotissue, the method including a step of clearing a fixed biotissue by contacting the fixed biotissue with the composition.

Advantageous Effects

The composition for clearing a biotissue and the method for clearing a biotissue using the same according to the present invention do not need expensive electrophoresis equipment and expensive solutions, and not only can be applied to various biotissues such as the brain, liver, lungs, kidneys, intestines, heart, muscle, and blood vessels, without damaging any of the biotissues, but also can improve the clarity of the biotissue without bubble formation, discoloration, and dark sediment, and enable antibody staining in the cleared tissues, so that the composition and the method can be usefully used to elucidate the causes of various diseases by the structural images of the biotissue and to establish a treatment method for a disease.

MODES OF THE INVENTION

Figure 1:
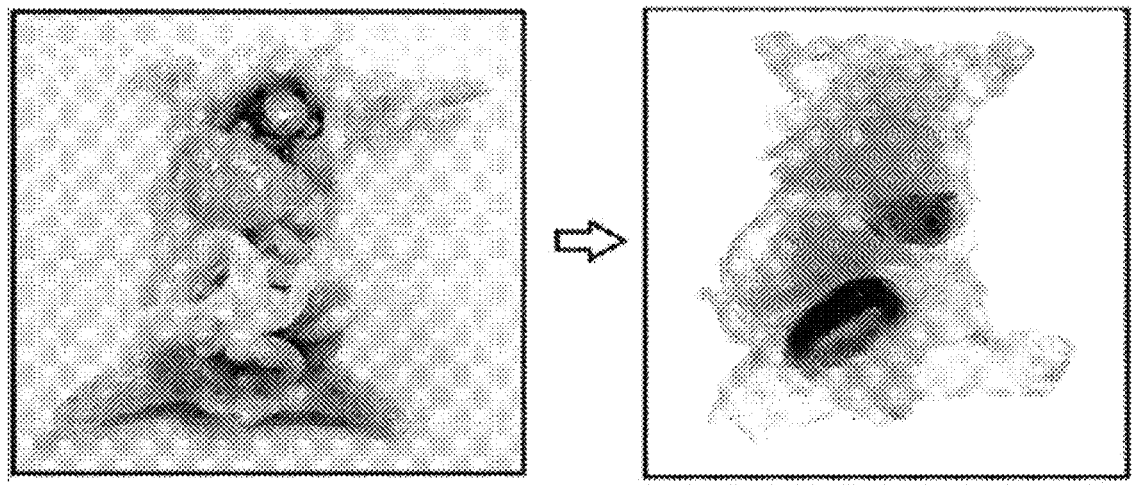
FIG. 1 is an image of an entire mouse tissue cleared by a method for clearing a tissue according to the present invention, and it can be seen that the right image in FIG. 1 in which the method for clearing a tissue according to the present invention is performed shows that the entire mouse tissue is relatively remarkably cleared as compared to the left image in FIG. 1.

Hereinafter, the present invention will be specifically described.
The present invention provides a composition for clearing a biotissue, comprising an amino acid represented by the following Formula 1, or a salt thereof.

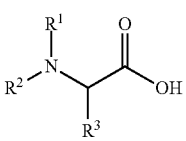

[Formula 1]

in Formula 1, $R^1$ is hydrogen or a $C_1$-$C_2$ alkyl, $R^2$ is hydrogen or a straight-chained or branched $C_8$-$C_{20}$ alkylcarbonyl or $C_8$-$C_{20}$ alkenylcarbonyl, and $R^3$ represents a side chain of an essential amino acid.

Hereinafter, the composition for clearing a biotissue according to the present invention will be more specifically described.

The composition for clearing a biotissue according to the present invention includes the amino acid represented by Formula 1 or a salt thereof, which removes the lipid component that blocks transmission of light and other molecules from the biotissue, does not cause structural degradation of the protein, and serves to harden the tissue.

In this case, in Formula 1, $R^1$ is hydrogen or a $C_1$-$C_2$ alkyl, $R^2$ is hydrogen or a straight-chained or branched $C_8$-$C_{20}$ alkylcarbonyl or $C_8$-$C_{20}$ alkenylcarbonyl, and $R^3$ represents a side chain of an essential amino acid.

Here, the "straight-chained or branched $C_8$-$C_{20}$ alkenylcarbonyl" refers to a carbonyl of an alkyl chain including at least one double bond and having 8 to 20 carbon atoms, and the "side chain of an essential amino acid" refers to a substituent which employs $NH_2(COOH)CH-$ as a backbone in 20 amino acids typically referred to as essential amino acids, that is, valine, leucine, isoleucine, methionine, phenylalanine, asparagine, glutamic acid, aspartic acid, glycine, alanine, serine, threonine, cysteine, proline, glutamine, histidine, lysine, arginine, tyrosine, and tryptophan. For example, a side chain of valine is hydrogen, and a side chain of alanine is methyl.

More preferably, the composition for clearing a biotissue according to the present invention may include an amino acid or a salt thereof, in which $R^1$ is methyl, $R^2$ is a straight-chained or branched $C_8$-$C_{20}$ alkylcarbonyl, and $R^3$ is hydrogen in Formula 1.

Further, in the composition for clearing a biotissue according to the present invention, the amino acid represented by Formula 1, or a salt thereof may be comprised at a concentration of 4 to 55 w/v % (weight/volume %), a concentration of 10 to 50 w/v % is preferred, and a concentration of 35 to 45 w/v % is more preferred.

In this case, although a solution for indicating the concentration may be a simulated body fluid typically used in the art, phosphate-buffered saline (PBS), Tris-buffered saline (TBS), distilled water, and the like are preferred, but the solution is not limited thereto.

When the amino acid represented by Formula 1, or a salt thereof is comprised at a concentration of less than 4 w/v %, the clearing speed of the biotissue may be remarkably decreased, and when the amino acid represented by Formula 1, or a salt thereof is comprised at a concentration of more than 55 w/v %, the amino acid represented by Formula 1, or a salt thereof may not be completely dissolved.

Furthermore, the composition for clearing a biotissue according to the present invention may further comprise a material which serves to rapidly promote the clearing of the biotissue by adjusting osmotic pressure. Preferred examples thereof comprise urea, 3-[(3-Cholamidopropyl)dimethylammonio]-1-propanesulfonate) (CHAPS), 3-[(3-Cholamidopropyl)dimethylammonio]-2-hydroxy-1-propanesulfonate) (CHAPSO), sucrose, fructose, glycerol, diatrizoic acid, t-octylphenoxypolyethoxyethanol (Triton X-100), polyoxyethylene (20) sorbitan monolaurate (Tween-20), 2-2-thiodiethanol, iohexol, and the like.

In this case, the material which rapidly promotes the clearing of the biotissue may be included at a concentration of 20 to 60 w/v %, and it is preferred that the material is included at a concentration of 30 to 50 w/v %. When the concentration is less than 20 w/v %, the clearing speed of the tissue may be decreased, and when the concentration is more than 60 w/v %, crystals may be caused or the amino acid represented by Formula 1, or a salt thereof may not be dissolved in the solution.

In addition, the concentration of the material which rapidly promotes the clearing of the biotissue may be appropriately adjusted with a preferred concentration range of the amino acid represented by Formula 1, or a salt thereof.

In order to use a clearing method in the related art, although a mounting solution needs to be additionally purchased and manufactured to match the refractive indices of the tissue and the solution, the composition for clearing a biotissue according to the present invention does not need a solution which matches the refractive indices, showing an effect of reducing costs.

As described above, the composition for clearing a biotissue according to the present invention does not need expensive electrophoresis equipment and expensive solutions, and not only can be applied to various biotissues such as the brain, liver, lungs, kidneys, intestines, heart, muscle, and blood vessels, without damaging any of the biotissues, but also can improve the clarity of the biotissue without bubble formation, discoloration, and dark sediment, and thus, may be usefully used as a composition for clearing a biotissue.

Further, the present invention provides a method for clearing a biotissue, the method comprising a step of clearing a fixed biotissue by contacting the fixed biotissue with the composition.

Hereinafter, a method for clearing a biotissue according to the present invention will be specifically described.

The method for clearing a biotissue according to the present invention comprises a step of clearing a fixed biotissue by contacting the fixed biotissue with the composition.

Specifically, the method for clearing a biotissue according to the present invention changes physicochemical characteristics of the biotissue and clears the biotissue by bringing a fixed biotissue into contact with a composition including the amino acid represented by Formula 1 or a salt thereof as an active ingredient, so that the biotissue is cleared by making light penetrate deeper into the biotissue.

The method for clearing a biotissue according to the present invention improves the clarity of the biotissue without bubble formation, discoloration, and dark sediment and does not cause the information in a desired tissue to be lost or distorted by the protein degradation, and the like, so that the information in the tissue may be detected and usefully used by using various fluorophores such as a GFP protein.

In addition, in the method for clearing a biotissue according to the present invention, although a biotissue may be applied and fixed without particular limitation as long as the method fixes the biotissue without typically causing the loss of antigenicity before the biotissue is cleared, the biotissue may be fixed by a typical method using paraformaldehyde (PFA), ethylene glycol diglycidyl ether, dipropylene glycol diglycidyl ether, 1,4-butanediol diglycidyl ether, glycerol polyglycidyl ether, glutaraldehyde, polyacrylamide, and the like.

Furthermore, in the method for clearing a biotissue according to the present invention, a pre-treatment step for dehydrating the biotissue may be further performed, and the pre-treatment step may be used without particular limitation as long as the step is typically a pre-treatment method for dehydrating a biotissue, but it is preferred that the fixed biotissue is impregnated with a solution in which the amino acid represented by Formula 1 is dissolved at a concentration of 20 to 50 w/v %, and it is more preferred that the fixed biotissue is impregnated with a solution in which the amino acid represented by Formula 1 is dissolved at a concentration of 35 to 45 w/v %. When the concentration of the pre-treatment solution is less than 20 w/v %, dehydration is not effectively performed, so that a swelling phenomenon of the tissue occurring during the clearing of the tissue may occur, and when the concentration is more than 50 w/v %, the amino acid represented by Formula 1 or a salt thereof is not completely dissolved, and the dehydration effect is not further enhanced.

In this case, although the solution showing the concentration may be a simulated body fluid typically used in the art, phosphate-buffered saline (PBS), Tris-buffered saline (TBS), distilled water, t-octylphenoxypolyethoxyethanol (Triton X-100), polyoxyethylene (20) sorbitan monolaurate (Tween-20), 3-[(3-Cholamidopropyl)dimethylammonio]-1-propanesulfonate) (CHAPS), 3-[(3-Cholamidopropyl)dimethylammonio]-2-hydroxy-1-propanesulfonate) (CHAPSO), and the like are preferred, but the solution is not limited thereto. Further, the temperature of impregnation is preferably 40 to 60° C., but is not limited thereto.

The pre-treatment process increases structural binding strength of a fixation material and a protein, does not cause degradation, and further hardens the tissue, prevents the swelling of the tissue occurring during the process of clearing the tissue, and may prevent the cracking of the tissue occurring in the antibody treatment process, the washing process, and the like.

The method for clearing a biotissue according to the present invention may be applied to tissues of various vertebrates, and particularly, it is preferred that the method is applied to the brain, blood vessels, liver, lungs, kidneys, pancreas, intestines, and the like, and the method may clear the entire part of the biotissue at one time.

Furthermore, the present invention provides a method for detecting important information in the cleared biotissue, that is, DNA, RNA, a protein, a fluorescent signal, and the like.

A cleared biotissue according to the present invention may detect a protein or mRNA through GFP fluorescence and immunostaining. Since the protein forms a network while forming covalent bonds between amino groups present in an amino acid during the fixation, the protein is very stable, whereas a nucleic acid such as RNA or DNA is relatively unstable even in a fixed tissue because an amino acid is not present in the nucleic acid. In particular, when an electrophoresis process is included, there is a risk that the position in the tissue is changed by electrical properties of the nucleic acid. In contrast, in the cleared biotissue according to the present invention, fluorescence staining is performed excellently on green fluorescent protein (GFP) cells and tyrosine hydroxylase as a dopaminergic neuron activity marker antibody.

Since the 3D distribution of cells and molecules of the biotissue which has not been damaged may be imaged and observed by the method for clearing a biotissue according to the present invention, an observation study may be performed by using a size of several micrometers or more from one complete structure for various biotissues having complex structures, so that the method may be effectively used to elucidate the causes of various diseases such as brain disease by obtaining useful information in the tissue.

Hereinafter, the present invention will be described in detail with reference to Examples and Experimental Examples.

However, the following Examples and Experimental Examples are only for exemplifying the present invention, and the content of the present invention is not limited by the following Examples and Experimental Examples.

EXPERIMENTAL EXAMPLE 1

Clearing of Biotissue 1

In order to clear a biotissue by using a composition according to the present invention, an experiment was performed as follows.

All animal experimental procedures were performed in accordance with the guidelines of the Animal Resource Committee of Keimyung University (Approval No. KM-2014-20R1).

First, adult mice (8 weeks old) were anesthetized by using a mixture of tiletamine, zolazepam, and xylazine, and Lectin-488 (Cat #DL1174) was injected into the tail veins of the mice in order to stain the blood vessels of the mice. After waiting for 5 minutes after the injection of Lectin, transcardial perfusion of 50 mL of ice-cold 1× phosphate-buffered saline was carried out, followed by perfusion of PBS including ice-cold 4% PFA. Subsequently, organs were harvested and immersed in a 4% PFA solution, followed by incubation at 4° C. for 12 hours.

Next, the sample was transferred to room temperature, further incubated for 2 hours, and washed twice with 50 ml of PBS. The fixed sample was incubated at a temperature of 55° C. and 220 rpm in a mixed solution of 4 w/v % N-sodium lauroyl sarcosinate and 60 w/v % urea for 3 days, and the results thereof are illustrated in FIG. 2.

Figure 2A:
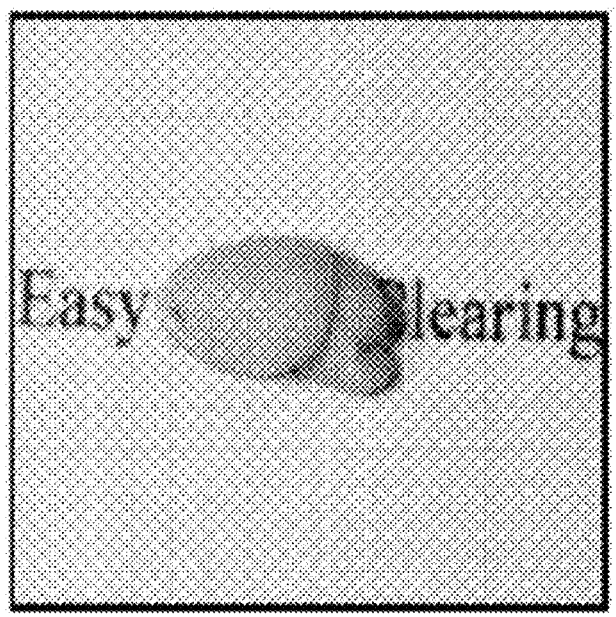
FIG. 2A is a mouse brain (half brain) before clearing the brain.
Figure 2B:
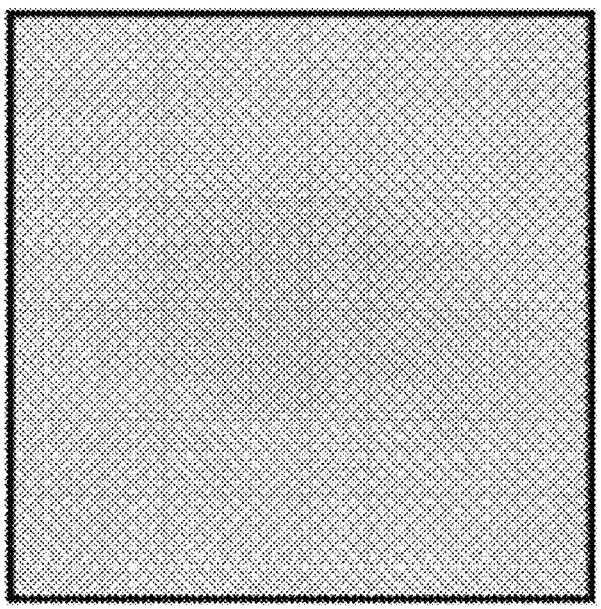
FIG. 2B is a mouse brain cleared through Experimental Example 1.

FIG. 2A is a mouse brain (half brain) before clearing the brain, and FIG. 2B is a mouse brain cleared through Experimental Example 1.

Accordingly, it can be seen that the mixed solution of N-sodium lauroyl sarcosinate and urea according to the present invention clears the biotissue.

EXPERIMENTAL EXAMPLE 2

Clearing of Biotissue 2

In order to clear a biotissue by using a composition according to the present invention, an experiment was performed as follows.

Specifically, the fixed sample in Experimental Example 1 was incubated at a temperature of 55° C. and 220 rpm in a mixed solution of 4 w/v % N-sodium lauroyl sarcosinate and 60 w/v % urea for 3 days, and further incubated at a temperature of 55° C. and 220 rpm in a mixed solution of 15 w/v % N-sodium lauroyl sarcosinate and 50 w/v % urea for 2 days.

It can be seen that the sample is more hardened and more cleared than the cleared tissue in Experimental Example 1.

EXPERIMENTAL EXAMPLE 3

Clearing of Biotissue 3

In order to clear a biotissue by using a composition according to the present invention, an experiment was performed as follows.

Specifically, an experiment was performed in the same manner as in Experimental Example 1, except that a pre-treatment process of treating the fixed sample in Experimental Example 1 with 40 w/v % N-sodium lauroyl sarcosinate prepared in advance for 12 hours was further performed, and the results thereof are illustrated in FIGS. 1 and 3 to 5.

FIG. 1 is an image of a cleared entire mouse tissue.

Figure 3A:
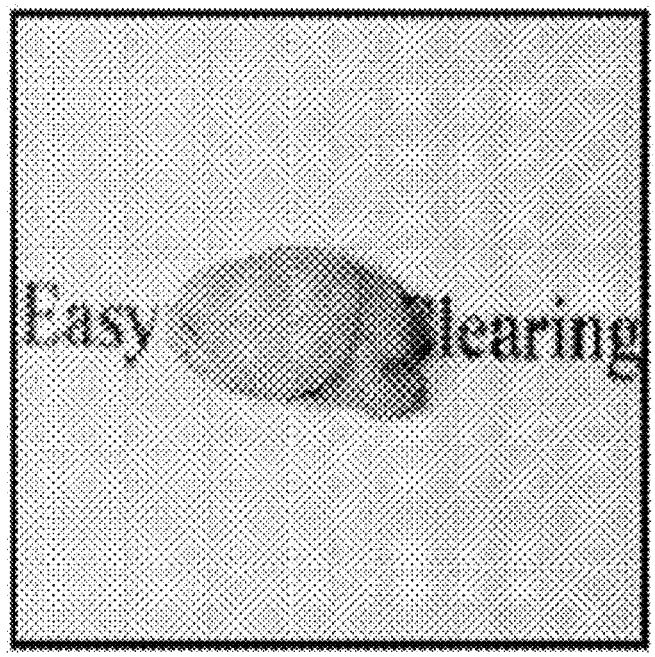
FIG. 3A is a mouse brain (half brain) before clearing the brain.
Figure 3B:
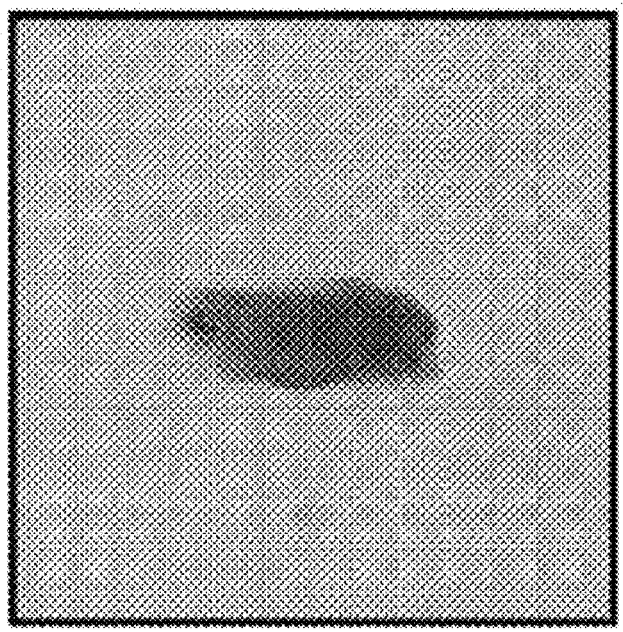
FIG. 3B is a mouse brain after pre-treatment with a 40 w/v/% N-lauroyl sarcosine solution in Experimental Example 3.
Figure 3C:
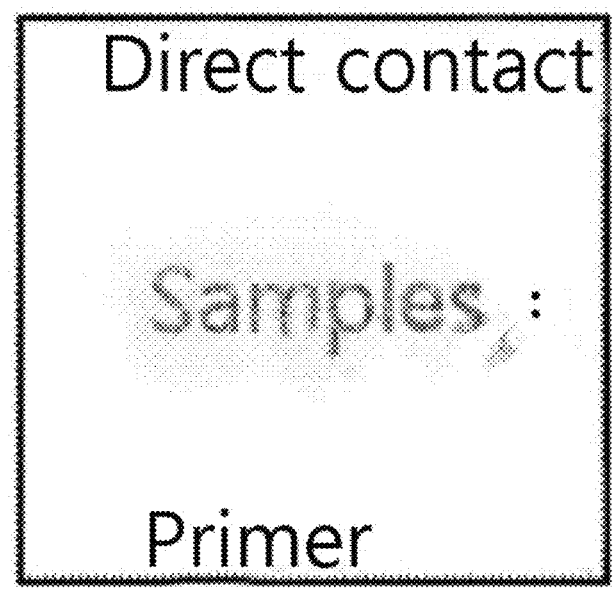
FIG. 3C is a mouse brain cleared through Experimental Example 3, and it can be seen that as the mouse brain is cleared, letters at the rear side of the mouse brain can be recognized by the unaided eye.

FIG. 3A is a mouse brain (half brain) before clearing the brain, FIG. 3B is a mouse brain after a pre-treatment with a 40 w/v/% N-lauroyl sarcosine solution in Experimental Example 3, and FIG. 3C is a mouse brain finally cleared through Experimental Example 3.

Figure 4A:
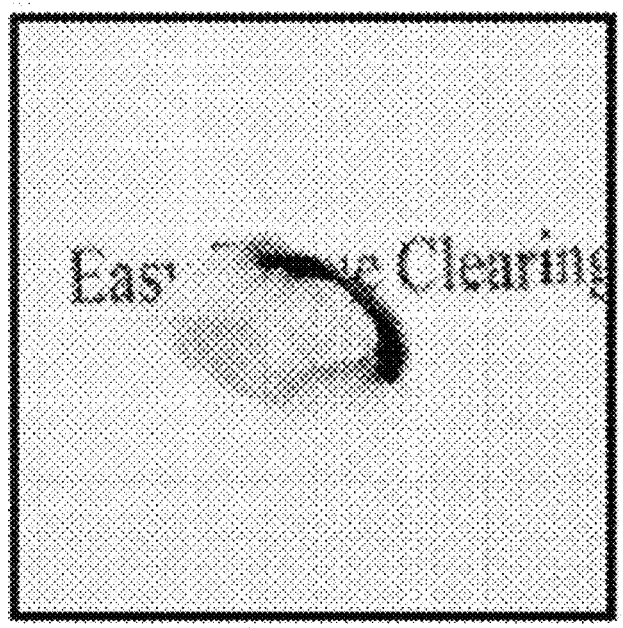
FIG. 4A is mouse pancreas.
Figure 4B:
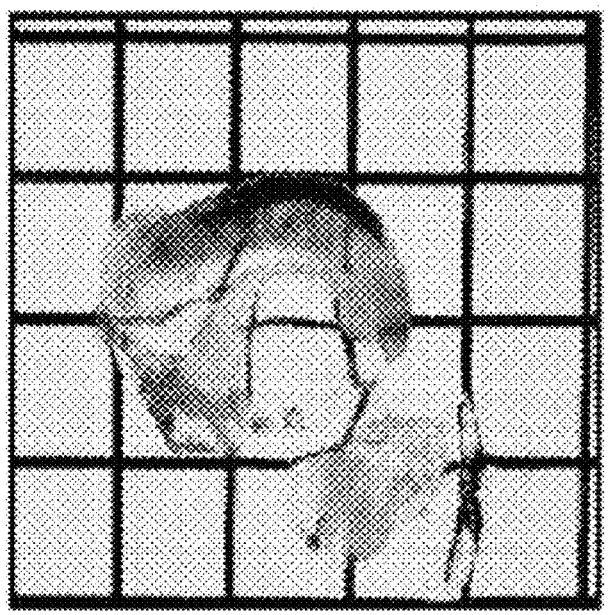
FIG. 4B is mouse pancreas finally cleared through Experimental Example 3, and it can be seen that the mouse pancreas is cleared.

FIG. 4A is mouse pancreas, and FIG. 4B is mouse pancreas finally cleared through Experimental Example 3.

Figure 5A:
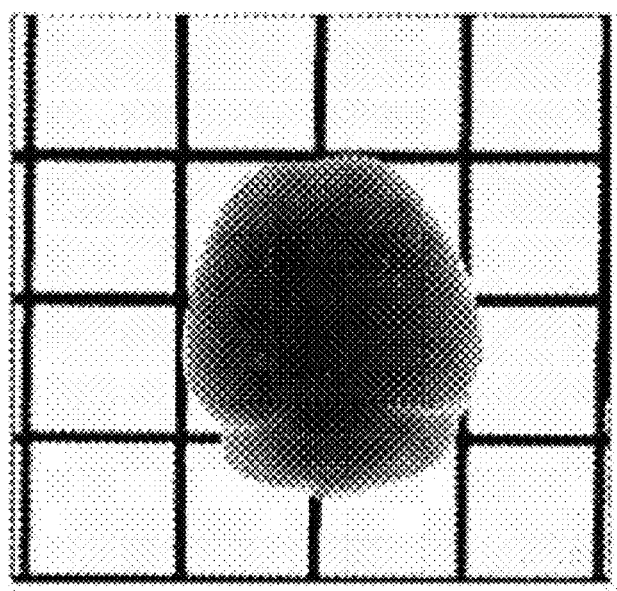
FIG. 5A is an image of an entire brain in a PBS solution before clearing the brain.
Figure 5B:
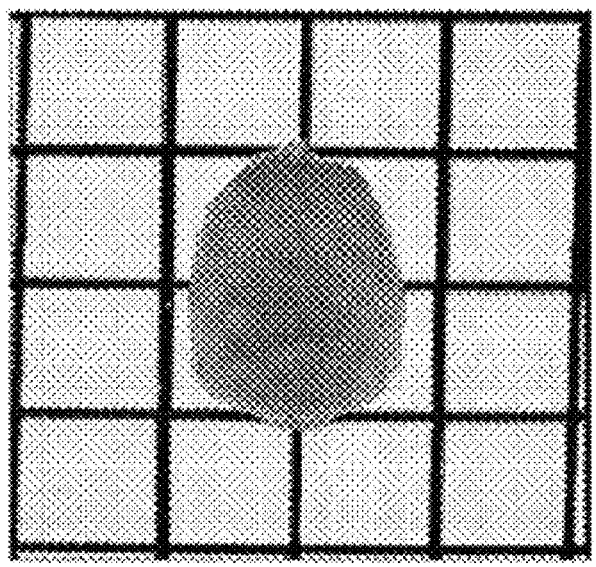
FIG. 5B is an image of an entire mouse brain in a 40 w/v/% N-lauroyl sarcosine solution in Experimental Example 3.
Figure 5C:
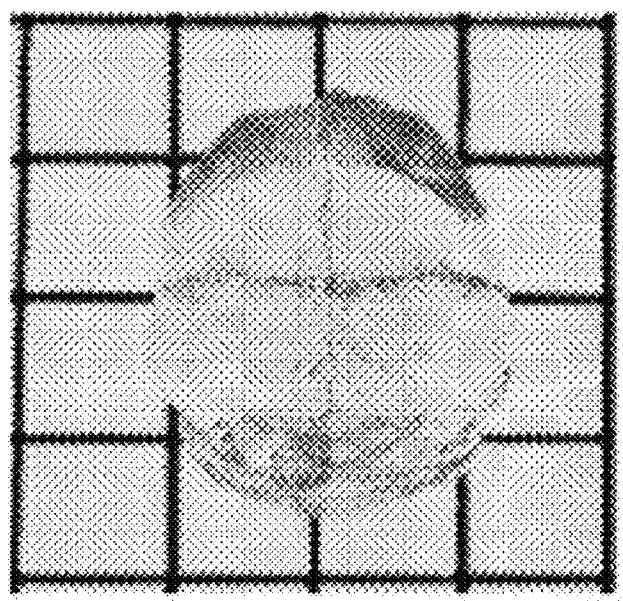
FIG. 5C is an entire mouse brain finally cleared through Experimental Example 3, and it can be confirmed that the mouse brain is cleared.

FIG. 5A is an entire brain in a PBS solution before clearing the brain, FIG. 5B is an entire mouse brain in a 40 w/v/% N-lauroyl sarcosine solution in Experimental Example 3, and FIG. 5C is an entire mouse brain finally cleared through Experimental Example 3.

As illustrated in FIGS. 1 and 3 to 5, the cleared entire tissue and the cleared brain and pancreas of the mouse can be confirmed. Therefore, it can be seen that the clearing method according to the present invention is optimal for clearing the biotissue perfectly.

EXPERIMENTAL EXAMPLE 4

Confirmation of Cleared Brain and Pancreatic Images of Adult Mice

In order to confirm the blood vessels of the cleared brain and pancreas by the clearing method according the present invention, GFP signals were confirmed by immunostained images of the mouse brain and pancreas using 5× and 20× objective lenses in the Selective Plane Illumination MicroscopyLightsheet Z.1.

Figure 10:
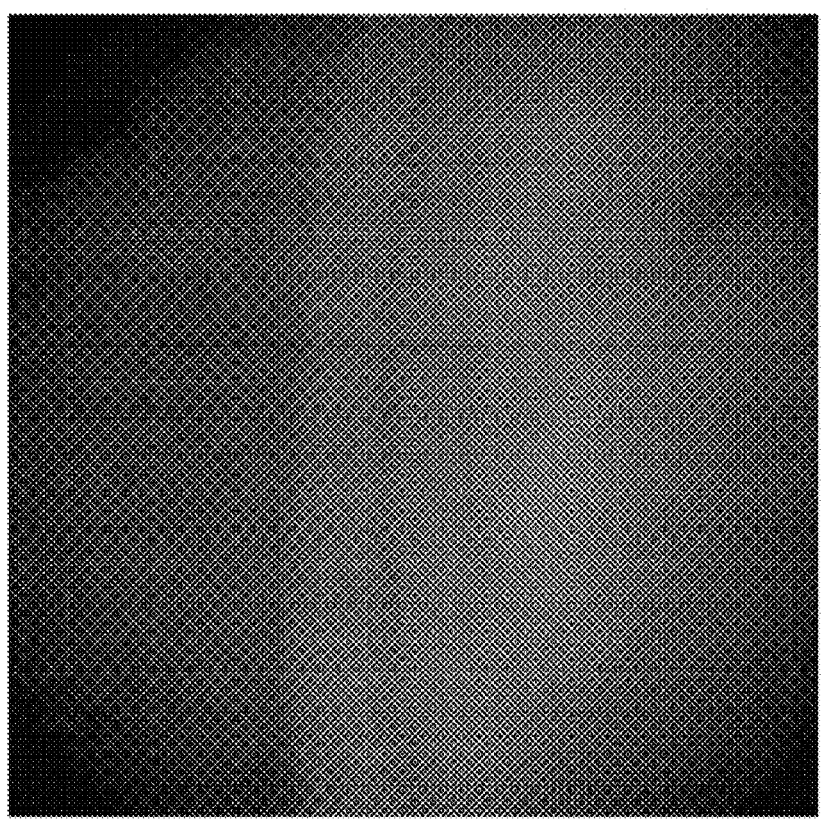
FIG. 10 is a partial image of video image data of inhibitory neuron-GFP.

Specifically, the cleared tissue in Experimental Example 2 was replaced three times in 50 mL of distilled water and incubated for 12 hours. Thereafter, the sample was put into a solution in which tyrosine hydroxylase (Cat #ab112) as a dopaminergic neuron activity marker antibody was mixed with 1% Triton X-100 and a PBS solution, and incubated at 4° C. for 3 days. After 3 days, the sample was washed again with distilled water for 12 hours, and then incubated at 4° C. in Donkey Anti-Rabbit IgG Alexa Fluor-594 for 3 days, and washed with 1× PBS for 6 hours. The sample subjected to washing was put into a mixed solution of N-lauroyl sarcosine and urea, incubated for 12 hours, and then measured by the Selective Plane Illumination MicroscopyLightsheet Z.1, immunostained images and GFP signals were confirmed by reconstructing 3D images in the Zeiss software, and the results thereof are illustrated in FIGS. 6 and 10. The imaging (Z-stack volume) enabled observation up to 0.6 mm to 3 mm.

Figure 6A:
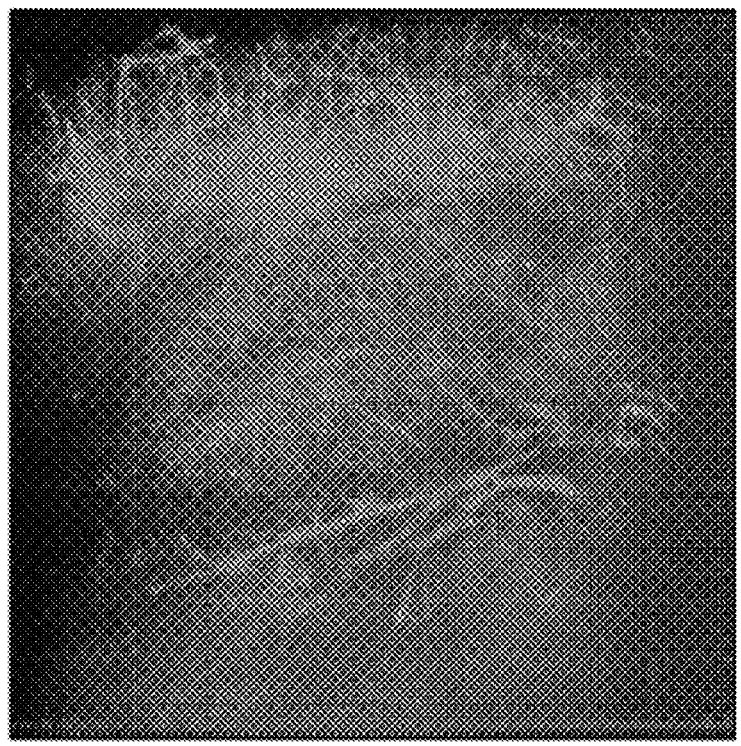
FIG. 6A is a Lectin-488 image of a mouse brain, and it can be seen that a green staining image is easily confirmed because the mouse brain is cleared.
Figure 6B:
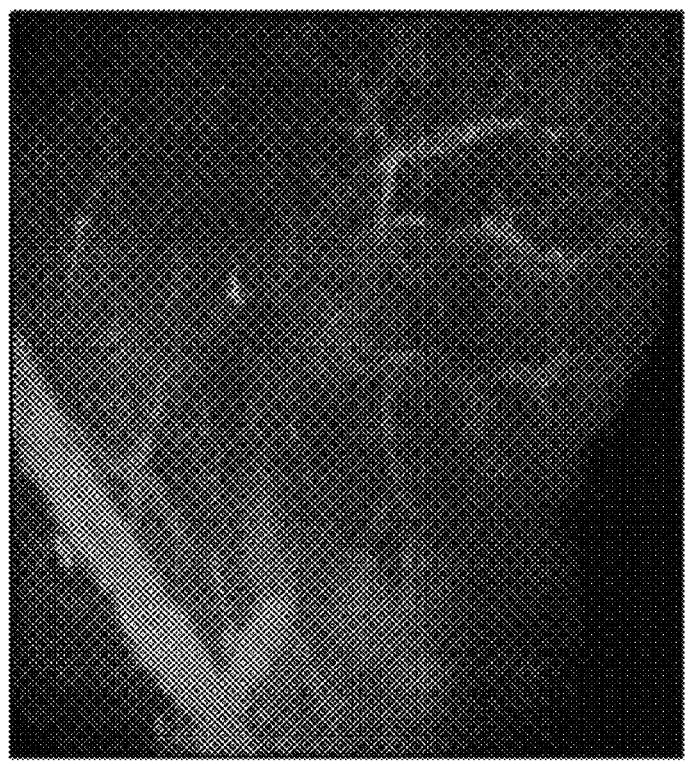
FIG. 6B is a Lectin-488 image of a mouse pancreas, and it can be seen that a green staining image is easily confirmed because the mouse pancreas is cleared.

FIG. 6A is a Lectin-488 image of a mouse brain, and FIG. 6B is a Lectin-488 image of a mouse pancreas.

Figure 7A:
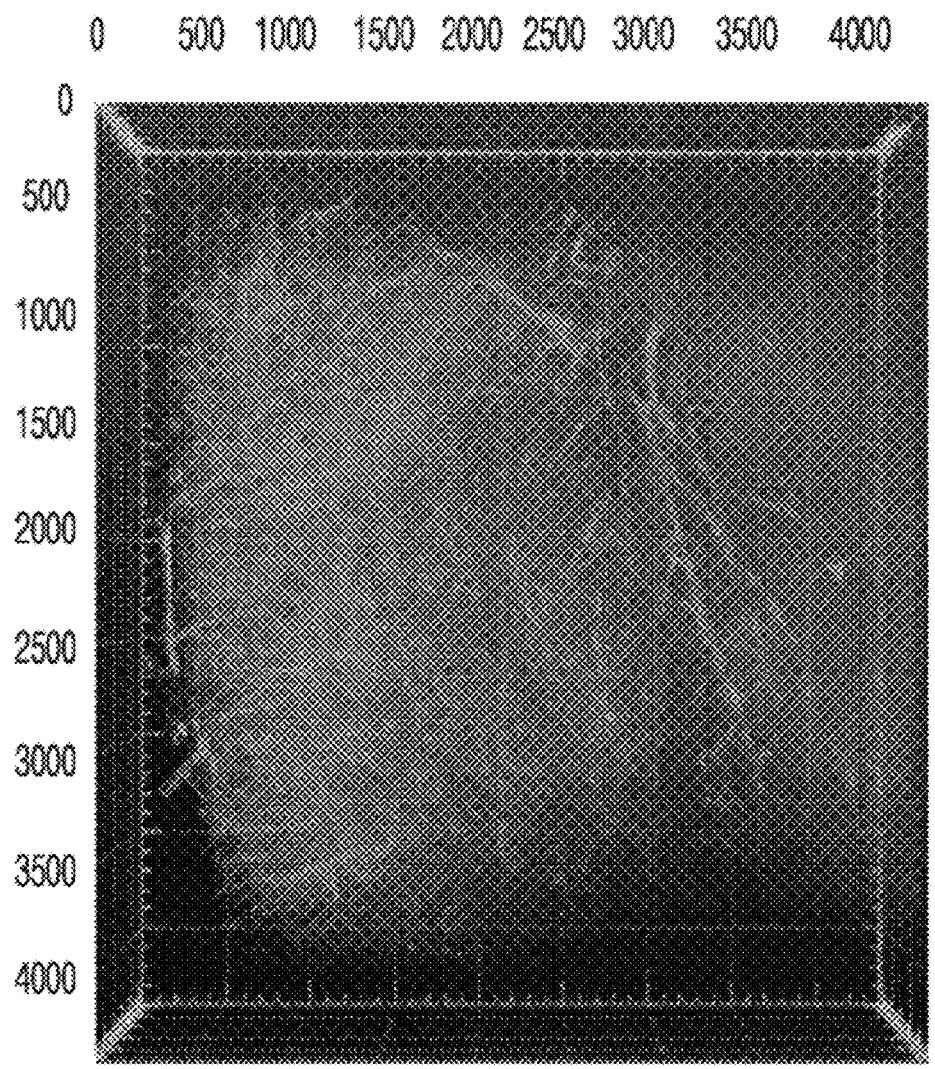
FIG. 7A is a Lectin-488 image of brain blood vessels, and it can be seen that a green staining image is easily confirmed because the brain is cleared.
Figure 7B:
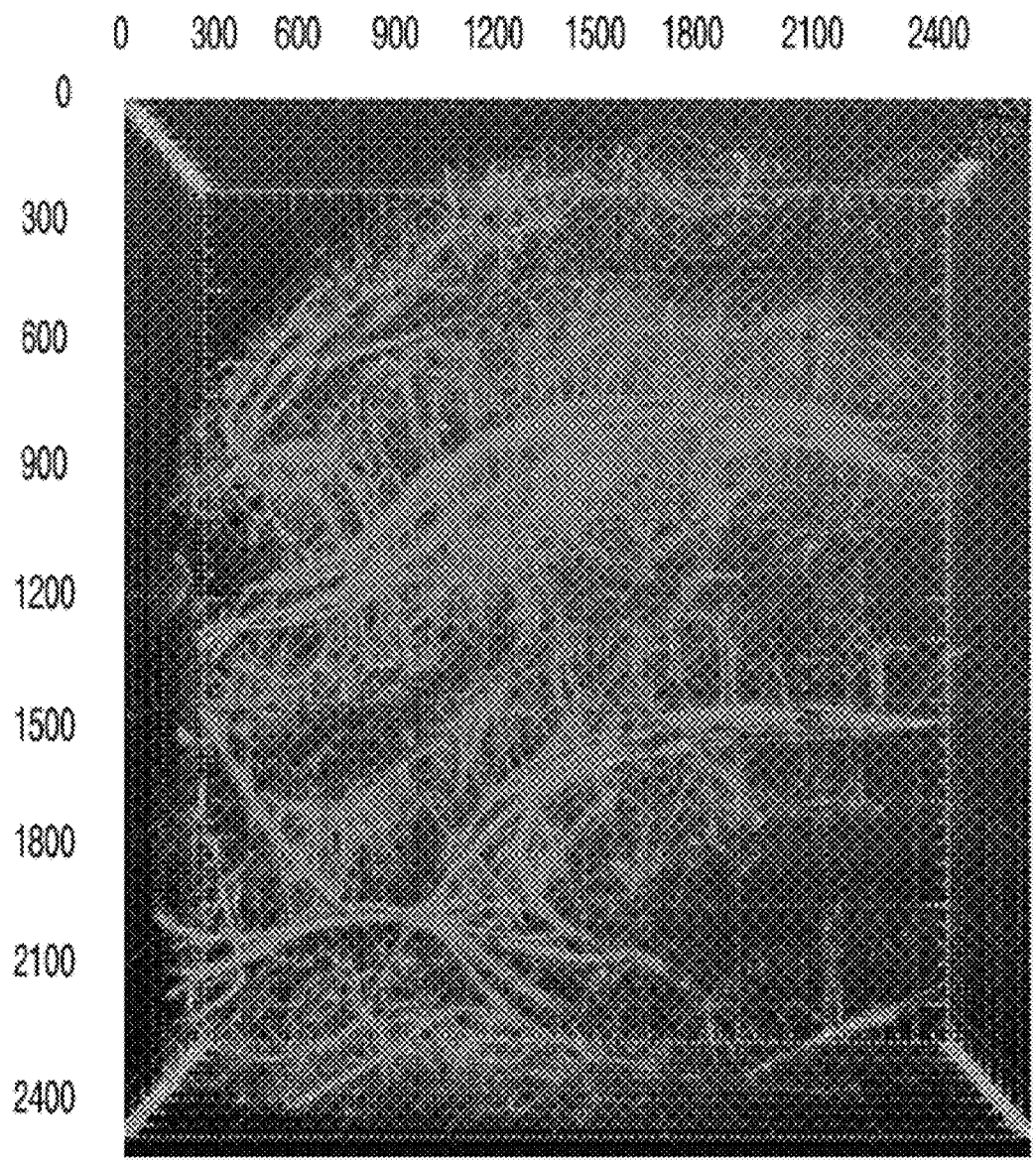
FIG. 7B is a Lectin-488 image of cerebellar blood vessels, and it can be seen that a green staining image is easily confirmed because the cerebellum is cleared.
Figure 7C:
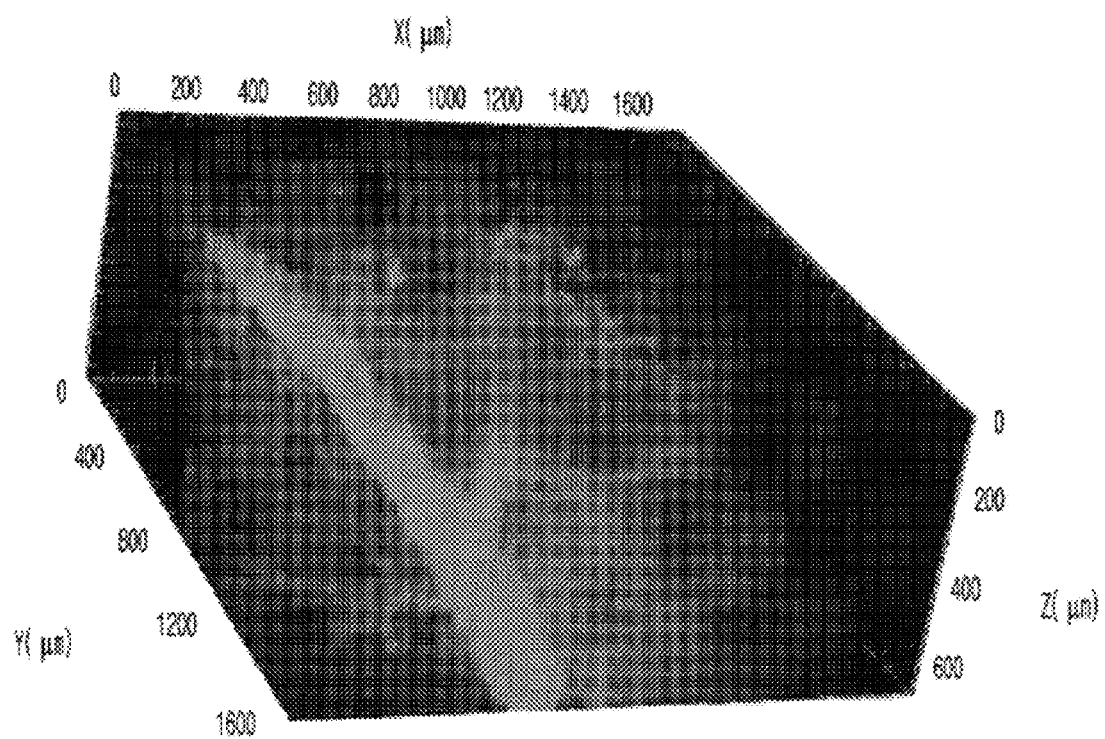
FIG. 7C is a Lectin-488 image of pancreatic blood vessels, and it can be seen that a green staining image is easily confirmed because the pancreas is cleared.

FIG. 7A is a Lectin-488 image of brain blood vessels, FIG. 7B is a Lectin-488 image of cerebellar blood vessels, and FIG. 7C is a Lectin-488 image of pancreatic blood vessels.

Figure 8A:
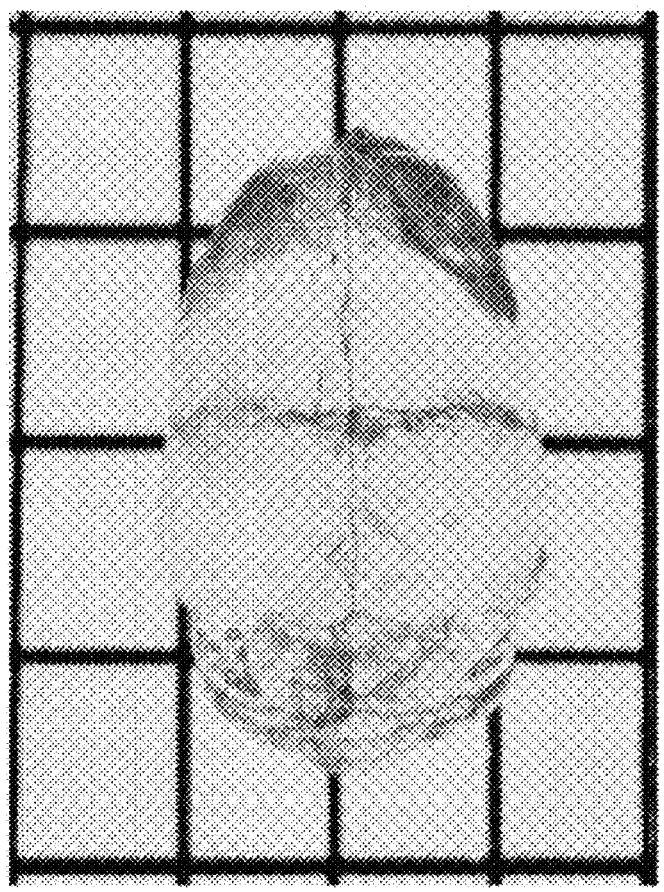
FIG. 8A is an image of a cleared entire mouse brain.
Figure 8B:
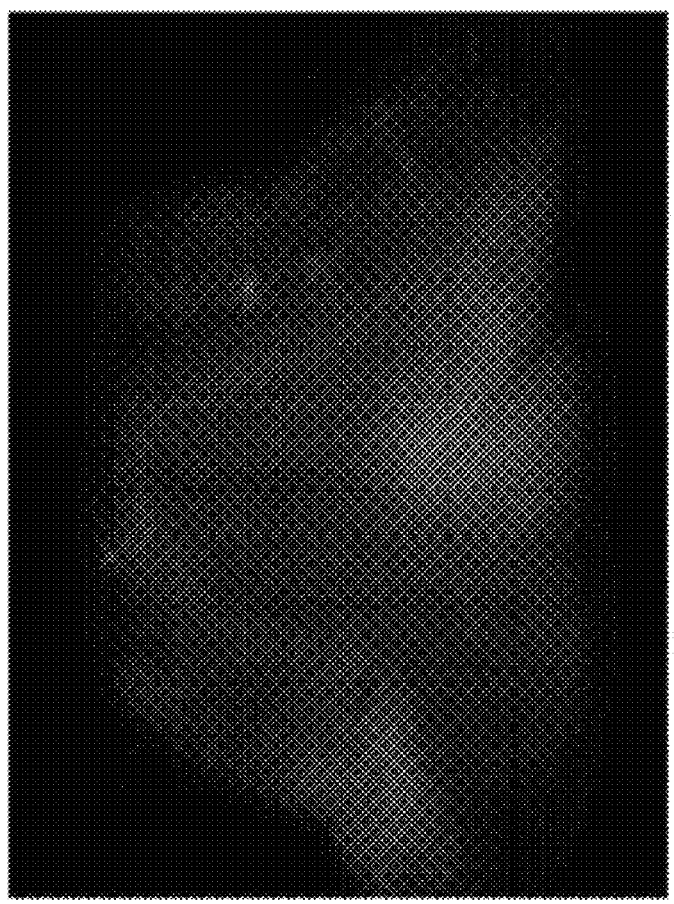
FIG. 8B illustrates a 5× microscope lens image for TH-antibody of the cleared entire brain.
Figure 8C:
FIG. 8C illustrates a 20× microscope lens image of inhibitory neuron-GFP present around the hippocampus.

FIG. 8A is an image of a cleared entire mouse brain, FIG. 8B is a 5× microscope lens image for TH-antibody of the cleared entire brain, and FIG. 8C is a 20× microscope lens image of inhibitory neuron-GFP present around the hippocampus.

Figure 9:
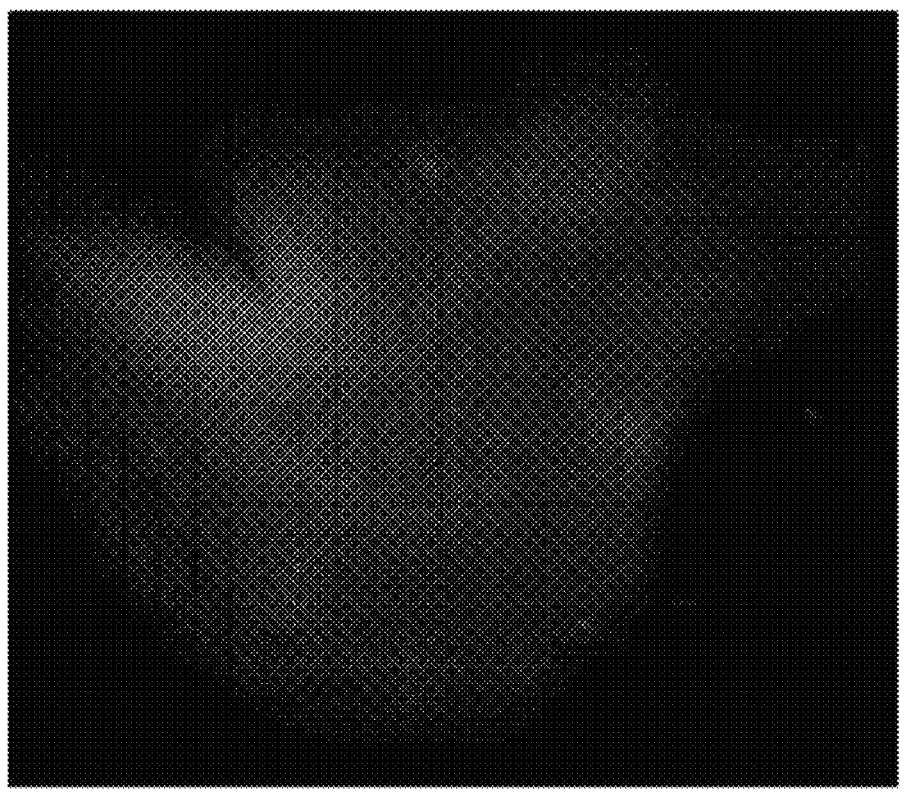
FIG. 9 is a partial image of video image data of TH-neuron.

FIG. 9 is a partial image of video image data of TH-neuron.

FIG. 10 is a partial image of video image data of inhibitory neuron-GFP.

As can be seen in FIGS. 6 to 10, the activated structure of the tissue could be visually confirmed by using a single-photon microscope after the tissue was cleared, and the blood vessel pattern could be three-dimensionally reconstructed. In particular, in the case of the blood vessel pattern of the imaged pancreas, it is very difficult to track a total pattern by general imaging and 3D reconstruction, but the method for clearing a tissue according to the present invention may provide 3D vascular system reconstruction and visual images.

Therefore, since the 3D distribution of cells and molecules of the biotissue which has not been damaged may be imaged and observed by the method for clearing a biotissue according to the present invention, an observation study may be performed with one complete structure for various biotissues having complex structures, so that the method may be effectively used for studies of pancreatic functions and brain disease by obtaining useful information in the tissue.

INDUSTRIAL APPLICABILITY

The composition for clearing a biotissue and the method for clearing a biotissue using the same according to the present invention do not need expensive electrophoresis equipment and expensive solutions, and not only can be applied to various biotissues such as the brain, liver, lungs, kidneys, intestines, heart, muscle, and blood vessels, without damaging any of the biotissues, but also can improve the clarity of the biotissue without bubble formation, discoloration, and dark sediment, and enable antibody staining in the cleared tissues, so that the composition and the method are useful for elucidating the causes of various diseases by the structural images of the biotissue and to establish a treatment method for a disease.

The invention claimed is:

1. A method for clearing a biotissue, the method comprising a step of clearing a fixed biotissue by contacting the fixed biotissue with a composition comprising an amino acid represented by Formula 1, or a salt thereof:

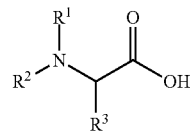

[Formula 1]

wherein $R^1$ is $CH_3$,
wherein $R^2$ is a straight-chained or branched $C_8$-$C_{20}$ alkylcarbonyl, and
wherein $R^3$ is H; and
wherein the composition further comprises one or more selected from the group consisting of urea, 3-[(3-Cholamidopropyl)dimethylammonio]-1-propanesulfonate) (CHAPS), 3-[(3-Cholamidopropyl)dimethylammonio]-2-hydroxy-1-propanesulfonate) (CHAPSO), sucrose, fructose, glycerol, diatrizoic acid, t-octylphenoxypolyethoxyethanol, polyoxyethylene (20) sorbitan monolaurate, 2-2-thiodiethanol, and iohexol.

2. The method of claim 1, wherein the fixed biotissue is a biotissue fixed using one or more selected from the group consisting of paraformaldehyde, ethylene glycol diglycidyl ether, dipropylene glycol diglycidyl ether, 1,4-butanediol diglycidyl ether, glycerol polyglycidyl ether, glutaraldehyde, and polyacrylamide.

3. The method of claim 1, wherein in the method, a step of pre-treating the fixed biotissue with the amino acid represented by Formula 1 of claim 1 is further performed before the step of clearing the fixed biotissue of claim 1, wherein the step of pre-treating the fixed biotissue is a step of dehydrating the fixed biotissue with 20 to 50 w/v % of the amino acid represented by Formula 1 of claim 1.

4. The method of claim 1, wherein the biotissue is the brain, blood vessels, liver, lungs, kidneys, pancreas, or intestinges.

5. The method of claim 1, wherein the composition comprises the amino acid in between about 4 and about 55 w/v %.

\* \* \* \* \*